(12) United States Patent
Liang et al.

(10) Patent No.: US 8,481,794 B2
(45) Date of Patent: Jul. 9, 2013

(54) METHODS AND APPARATUSES FOR PRODUCING ETHYLBENZENE

(75) Inventors: Wugeng Liang, Elgin, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 248 days.

(21) Appl. No.: 13/103,545

(22) Filed: May 9, 2011

(65) Prior Publication Data

US 2012/0289754 A1 Nov. 15, 2012

(51) Int. Cl.
*C07C 2/66* (2006.01)

(52) U.S. Cl.
USPC ........................... 585/467; 585/449

(58) Field of Classification Search
USPC .................................. 585/467, 449
See application file for complete search history.

(56) References Cited

U.S. PATENT DOCUMENTS

| | | | |
|---|---|---|---|
| 5,902,917 A | 5/1999 | Collins et al. | |
| 5,959,168 A | 9/1999 | van der Aalst et al. | |
| 6,096,935 A | 8/2000 | Schulz et al. | |
| 6,479,721 B1 | 11/2002 | Gajda et al. | |
| 6,984,764 B1 | 1/2006 | Roth et al. | |
| 7,297,827 B2 | 11/2007 | Kelly | |
| 7,652,181 B1 | 1/2010 | Schmidt et al. | |
| 2008/0171900 A1* | 7/2008 | Schmidt | 585/449 |
| 2008/0194897 A1 | 8/2008 | Clark et al. | |
| 2008/0242907 A1 | 10/2008 | Clark et al. | |

OTHER PUBLICATIONS

Borodina, I, et al., Hydroalkylation of benzene and ethylbenzene over metal containing zeolite catalysts, Microporous and Mesoporous Materials, v 105, n 1-2, p. 181-188, Sep. 15, 2007.

* cited by examiner

*Primary Examiner* — Thuan D Dang
(74) *Attorney, Agent, or Firm* — Mark R Willis

(57) ABSTRACT

Embodiments of methods and apparatuses for producing ethylbenzene are provided. The method comprises the steps of introducing a first feed mixture comprising benzene and ethylene to UZM-8 zeolite-based catalyst at a first predetermined inlet temperature to form a first intermediate outlet stream comprising ethylbenzene and benzene. Ethylene is added to the first intermediate outlet stream to form a second intermediate feed mixture. The second intermediate feed mixture is introduced to beta zeolite-based catalyst at a second predetermined inlet temperature to form ethylbenzene.

6 Claims, 1 Drawing Sheet

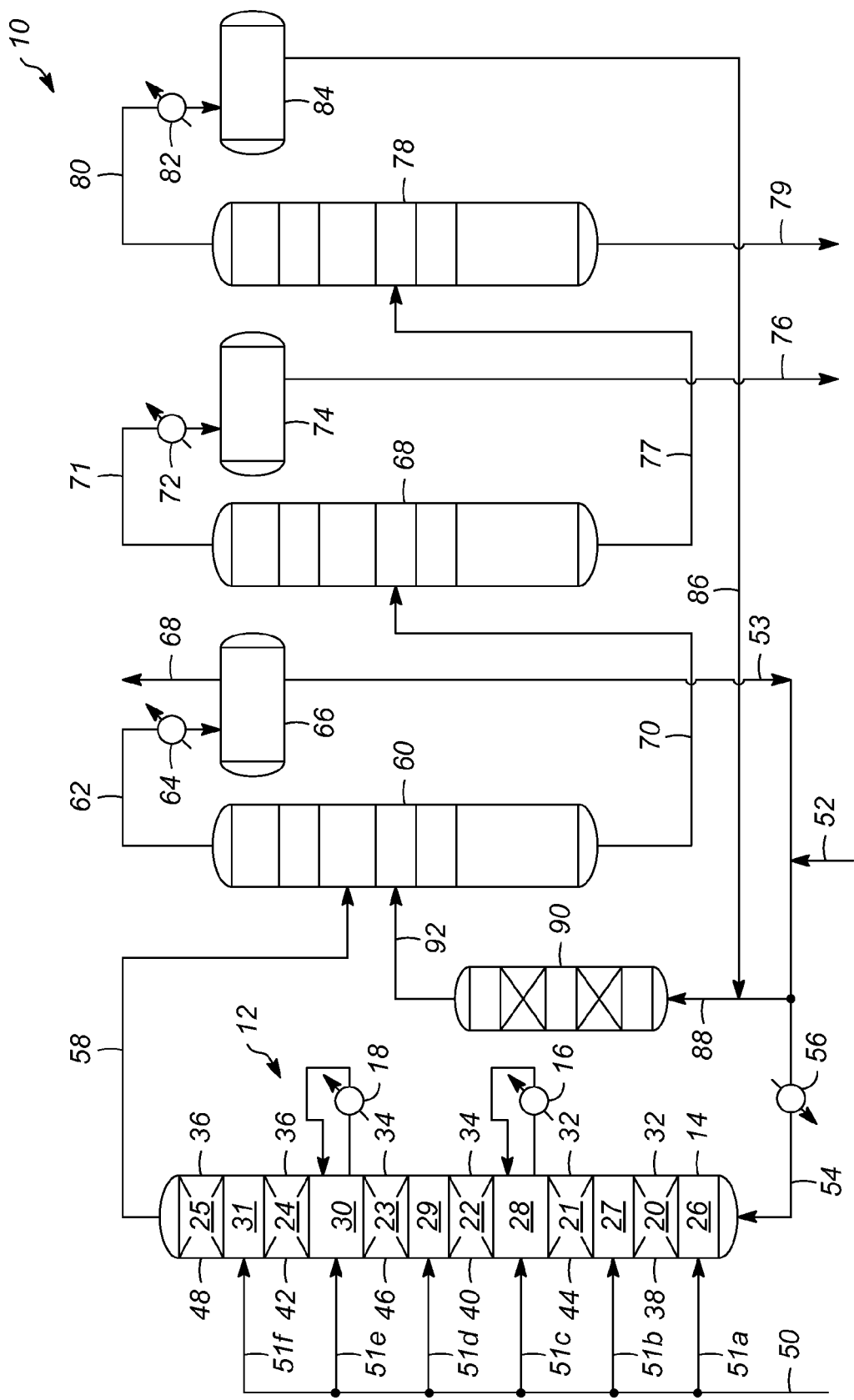

METHODS AND APPARATUSES FOR PRODUCING ETHYLBENZENE

FIELD OF THE INVENTION

The present invention relates generally to methods and apparatuses for producing monoalkylaromatics from olefins and aromatics, and more particularly to methods and apparatuses for producing ethylbenzene from ethylene and benzene.

BACKGROUND OF THE INVENTION

Catalytic alkylation processes are commonly used for the production of monoalkylaromatics from olefins and aromatics. One commercialized application of this process is for the conversion of ethylene and benzene to ethylbenzene that may subsequently be used, for example, to produce styrene.

The catalytic alkylation of benzene with ethylene to produce ethylbenzene is very exothermic and the associated ethylbenzene production systems need to manage the heat generated to control the product outlet temperatures of the reactors. If a reactor is built for higher outlet temperatures, its construction cost will be higher because more expensive materials are required to handle the higher temperatures. To control the outlet temperatures, many ethylbenzene production processes use reactors that have thermally-insulated catalytic sections with cooling provided between these sections to remove excess heat. Additionally, relatively high benzene to ethylene (BE) molar ratios for feeding benzene and ethylene, e.g., BE ratios of about 5 or 6, to the reactors are used. Because the feed is benzene-ultra-rich, high amounts of unreacted or excess benzene are available throughout the reactor to act as a heat sink to further control the rise in process temperatures. As a consequence of the excess benzene, the cost of many ethylbenzene production systems and the expense of their operation are high because larger reactors and more elaborate and expensive recycling sub-systems are required to handle the additional volume of benzene.

Recently, some of the ethylbenzene production apparatuses are being built to operate at lower inlet temperatures for operation at lower BE ratios for the introduction of benzene and ethylene into the catalytic sections of the reactors. Unfortunately, the various catalysts currently available for alkylation of benzene with ethylene either have relatively low activity or they deactivate rapidly at lower temperatures and need to be replaced more often. Because the cost of replacing a catalyst is very expensive, a less active and more stable catalyst is often used to reduce the frequency of catalyst replacement. Using a less active catalyst means that more catalyst must be used, thereby increasing cost, to achieve an equivalent yield of ethylbenzene that would otherwise be achieved using a more active catalyst.

Accordingly, it is desirable to provide methods and apparatuses for producing ethylbenzene using relatively low inlet temperatures and low BE ratios without the high cost associated with frequent catalyst replacement. Moreover, it is desirable to provide methods and apparatuses for producing relatively high yields of ethylbenzene using relatively low inlet temperatures and low BE ratios without the cost associated with using additional catalyst. Furthermore, other desirable features and characteristics of the present invention will become apparent from the subsequent Detailed Description of the Invention and the appended Claims, when taken in conjunction with the accompanying drawings and this Background of the Invention.

SUMMARY OF THE INVENTION

Methods and apparatuses for producing ethylbenzene are provided herein. In accordance with an exemplary embodiment, a method for producing ethylbenzene comprises the steps of introducing a first feed mixture comprising benzene and ethylene to UZM-8 zeolite-based catalyst at a first predetermined inlet temperature to form a first intermediate outlet stream comprising ethylbenzene and benzene. Ethylene is added to the first intermediate outlet stream to form a second intermediate feed mixture. The second intermediate feed mixture is introduced to beta zeolite-based catalyst at a second predetermined inlet temperature to form ethylbenzene.

In accordance with another exemplary embodiment, a method for producing ethylbenzene uses an alkylator apparatus that comprises at least one group of adjacent thermally-insulated catalyst beds where each of the at least one group of adjacent thermally-insulated catalyst beds includes a cold bed and a hot bed. The method comprises the steps of introducing a benzene stream and a plurality of ethylene streams to the alkylator apparatus at a predetermined benzene to ethylene (BE) ratio. The benzene stream is combined with a first ethylene stream to form a first feed mixture. A first feed mixture is contacted with UZM-8 zeolite-based catalyst in a first cold bed at conditions effective to form a first intermediate outlet stream comprising ethylbenzene and benzene. The first intermediate outlet stream is combined with a second ethylene stream to form a second intermediate feed mixture. The second intermediate feed mixture is contacted with beta zeolite-based catalyst in a first hot bed at conditions effective to form ethylbenzene.

In accordance with another exemplary embodiment, an alkylator apparatus for producing ethylbenzene comprises a reactor configured to receive a benzene stream and a plurality of ethylene streams including a first ethylene stream and a second ethylene stream. The reactor comprises a first group of adjacent thermally-insulated catalyst beds including a first cold bed and a first hot bed that contain UZM-8 zeolite-based catalyst and beta zeolite-based catalyst, respectively. The reactor is configured to combine the benzene stream with the first ethylene stream to form a first feed mixture that is fluidly communicated to the first cold bed at a first predetermined inlet temperature to form a first intermediate outlet stream. The first intermediate outlet stream is combined with the second ethylene stream to form a second intermediate feed mixture that is fluidly communicated to the first hot bed at a second predetermined inlet temperature to form a second outlet stream comprising ethylbenzene and benzene.

BRIEF DESCRIPTION OF THE DRAWINGS

Embodiments of the present invention will hereinafter be described in conjunction with the following drawing figures, wherein like numerals denote like elements, and wherein:

FIG. 1 schematically illustrates a system including an alkylator apparatus for producing ethylbenzene in accordance with an exemplary embodiment.

DETAILED DESCRIPTION

The following Detailed Description is merely exemplary in nature and is not intended to limit the invention or the application and uses of the invention. Furthermore, there is no intention to be bound by any theory presented in the preceding Description of Related Art or the following Detailed Description.

Various embodiments contemplated herein relate to methods and apparatuses for producing ethylbenzene. An alkylator apparatus comprises a reactor that is a multi-fixed bed flow reactor and is configured to receive a benzene stream and a plurality of ethylene streams at a predetermined benzene to ethylene (BE) ratio. Preferably, the BE ratio is relatively low and is about 3 or less. The reactor comprises at least one group of adjacent thermally-insulated catalyst beds. In particular, no external cooling is provided interposingly between the adjacent catalyst beds of the group. In an exemplary embodiment, the reactor comprises at least two groups of adjacent thermally-insulated catalyst beds and the alkylator apparatus further comprises a heat exchanger. The heat exchanger is configured to provide cooling to the intermediate reactant-product mixture between the two groups of adjacent thermally-insulated catalyst beds.

In the reactor upstream from the group of adjacent thermally-insulated catalyst beds is a first pre-bed space. The benzene stream is combined with one of the ethylene streams in the first pre-bed space to form a feed mixture that is benzene-rich. The group of adjacent thermally-insulated catalyst beds includes a cold bed and a hot bed. The hot bed is downstream from the cold bed and is operating at a higher temperature than the cold bed during production due to the exothermic conversion of benzene and ethylene to ethylbenzene. The cold bed initially receives the feed mixture at a first predetermined inlet temperature. In an exemplary embodiment, the first predetermined inlet temperature is about 190° C. or less, which is relatively low in comparison to conventional ethylbenzene production processes with beta zeolite catalyst.

The cold bed contains UZM-8 zeolite-based catalyst for the catalytic alkylation of benzene with ethylene present in the feed mixture. UZM-8 is a zeolitic material described in U.S. Pat. No. 6,756,030, which is incorporated herein by reference. As described, UZM-8 is a microporous crystalline zeolite having a layered framework of at least $AlO_2$ and $SiO_2$ tetrahedral units and a composition on an as-synthesized and anhydrous basis expressed by an empirical formula of:

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation: z=(mn+rp+3+4y)/2. From the UZM-8 zeolite, steps of forming, calcination, ion-exchange and final activation to prepare the catalyst for reaction are done. The inventors have found that although the UZM-8 zeolite-based catalyst does not have relatively high activity for the catalytic alkylation of benzene with ethylene, it has very low deactivation at relatively low inlet temperatures.

The feed mixture is advanced through the cold bed contacting the UZM-8 zeolite-based catalyst to form an intermediate outlet stream comprising ethylbenzene and unreacted benzene. The heat generated during the reaction causes an increase in temperature as the feed mixture is reacted and advanced through the cold bed to form the intermediate outlet stream. The intermediate outlet stream is advanced from the cold bed to a second pre-bed space and combined with a second ethylene stream to form an intermediate feed mixture that is introduced to the hot bed. In an exemplary embodiment, the intermediate feed mixture has a second predetermined inlet temperature of about 230° C. or less as it is introduced to the hot bed.

The hot bed contains beta zeolite-based catalyst for the catalytic alkylation of benzene with ethylene in the intermediate feed mixture. Beta zeolite or BEA is a zeolitic material that is described in D. W. Breck, ZEOLITE MOLECULAR SIEVES, John Wiley and Sons, New York, 1974. From the beta zeolite, steps of forming, calcination, ion-exchange and final activation to prepare the catalyst for reaction are done.

The intermediate feed mixture is advanced through the hot bed contacting the beta zeolite-based catalyst to form an outlet stream comprising ethylbenzene and some unreacted benzene. The heat generated during the reaction causes an increase in temperature as the intermediate feed mixture is reacted and advanced through the hot bed to form the outlet stream. In an exemplary embodiment, the outlet stream is at a temperature of about 260° C. or less.

The inventors have found that although the beta zeolite-based catalyst has relatively fast deactivation under low inlet temperatures, it is very active and is stable at the higher inlet and processing temperatures associated with the hot bed. Additionally, the amount of beta zeolite-based catalyst used in the hot bed is from about 30 to about 50% less in weight than the amount of UZM-8 zeolite-based catalyst used in the cold bed for producing equivalent yields of ethylbenzene because of the high activity of the beta zeolite-based catalyst. Therefore, by using UZM-8 zeolite-based catalyst that exhibits lower activity but very low deactivation under low inlet temperatures in the cold bed and using beta zeolite-based catalyst that exhibits faster deactivation under low inlet temperatures but very high activity and is stable at higher inlet temperatures in the hot bed, the reactor can be operated efficiently under relatively low BE feed ratios and low inlet temperatures. Moreover, the frequency of replacing the catalyst in the reactor is reduced in comparison to having used the beta zeolite-based catalyst in both the cold and hot beds. Furthermore, the amount of catalyst used overall is reduced in comparison to having used the UZM-8 zeolite-based catalyst in both the cold and hot beds.

Referring to FIG. 1, a schematic depiction of a system 10 for producing ethylbenzene from the alkylation of benzene with ethylene in accordance with an exemplary embodiment is provided. The system 10 comprises an alkylator apparatus 12 configured for the catalytic alkylation of benzene with ethylene to produce ethylbenzene. The alkylator apparatus 12 comprises a reactor 14 and a plurality of heat exchangers 16 and 18. The reactor 14 is shown as a multi-fixed bed upflow reactor, but a multi-fixed bed downflow reactor may also be used. The reactor 14 comprises multiple fixed catalyst beds 20, 21, 22, 23, 24, and 25 that are separated from each other by pre-bed spaces 26, 27, 28, 29, 30, and 31. The fixed catalyst beds 20, 21, 22, 23, 24, and 25 are grouped into three groups of adjacent thermally-insulated catalyst beds 32, 34, and 36 and process cooling is provided by the heat exchanger 16 between the first and second groups of adjacent thermally-insulated catalyst beds 32 and 34, and by the heat exchanger 18 between the second and third groups of adjacent thermally-insulated catalyst beds 34 and 36. Although the reactor 14 is shown as having three groups of adjacent thermally-insulated catalyst beds 32, 34 and 36, the reactor 14 may be configured with more than three groups or less than three groups.

The catalyst beds 20, 22, and 24 are the cold beds 38, 40, and 42 of the groups of adjacent thermally-insulated catalyst beds 32, 34, and 36, respectively. The catalyst beds 21, 23, and 25 are the hot beds 44, 46, and 48 of the groups of adjacent thermally-insulated catalyst beds 32, 34, and 36, respectively. In an exemplary embodiment, all of the cold beds 38, 40, and 42 contain UZM-8 zeolite-based catalyst and preferably, contain substantially no beta zeolite-based catalyst. The term "substantially no 'X' zeolite-based catalyst" as used herein means the 'X' zeolite-based catalyst, if present, is not used in an amount that measurably affects the catalytic alkylation of benzene with ethylene. In another exemplary embodiment, all of the hot beds 44, 46, and 48 contain beta zeolite-based catalyst and preferably, contain substantially no UZM-8 zeolite-based catalyst.

As illustrated, a stream of ethylene 50 is split into several portions that are introduced into the pre-bed spaces 26, 27, 28, 29, 30, and 31 of the reactor 14 via multiple lines 51a-f. A fresh stream of benzene 52 is combined with a recycled benzene stream 53, as will be discussed in further detail below, to form a benzene feed stream 54. The benzene feed stream 54 is cooled via a heat exchanger 56 and advanced into the first pre-bed space 26 of the reactor 14. In an exemplary embodiment, the benzene feed stream 54 and the ethylene stream 50 are introduced into the reactor 14 at a BE ratio of from about 1.5 to about 3.

The cooled benzene feed stream 54 is combined with a first portion of ethylene from line 51a in the first pre-bed space 26 of the reactor 14 to form a feed mixture at a first predetermined inlet temperature. In an exemplary embodiment, the first predetermined inlet temperature of the feed mixture is from about 160 to about 190° C. The feed mixture is introduced into the first cold bed 38 and contacts the UZM-8 zeolite-based catalyst to convert the ethylene and a portion of the benzene in the feed mixture to ethylbenzene to form a first intermediate outlet stream that is advanced into the pre-bed space 27. As is the case for the catalytic reactions in all of the catalyst beds 20, 21, 22, 23, 24, and 25, the reactions of ethylene with benzene are predominately alkylation reactions forming predominately ethylbenzene although some by-products are formed, such as, for example, polyethylbenzene (PEBs) including diethylbenzene, triethylbenzene, and butylbenzene. Accordingly, the first intermediate outlet stream comprises ethylbenzene, PEBs, and unreacted benzene.

The first intermediate outlet stream that has been heated by the exothermic reactions in the cold bed 38 is combined with a second portion of ethylene from line 51b in the second pre-bed space 27 of the reactor 14 to form a second intermediate feed mixture at a second predetermined inlet temperature. In an exemplary embodiment, the second predetermined inlet temperature of the second intermediate feed mixture is from about 190 to about 230° C. The second intermediate feed mixture is introduced into the first hot bed 44 and contacts the beta zeolite-based catalyst to convert the ethylene and a portion of the benzene in the second intermediate feed mixture to ethylbenzene to form a second intermediate outlet stream. The second intermediate outlet stream comprises ethylbenzene, PEBs, and unreacted benzene.

The second intermediate outlet stream has been heated by the exothermic reactions in the hot bed 44 to an intermediate outlet temperature of preferably not greater than about 260° C. To control the rising temperatures in the reactor 14, the second intermediate outlet stream is passed through and cooled in the heat exchanger 16 before being fluidly communicated into the third pre-bed space 28. The cooled second intermediate outlet stream is combined with a third portion of ethylene from line 51c in the third pre-bed space 28 to form a third intermediate feed mixture at a third predetermined inlet temperature. In an exemplary embodiment, the third predetermined inlet temperature is about the same temperature as the first predetermined inlet temperature or is from about 160 to about 190° C.

The third intermediate feed mixture is introduced into the second cold bed 40. The process is then repeated for the second and third groups of adjacent thermally-insulated catalytic beds 34 and 36 with interposing cooling between the groups 34 and 36 via the heat exchanger 18 as described above in relation to the first group of adjacent thermally-insulated catalyst beds 32 with cooling via the heat exchanger 16. At the third group of adjacent thermally-insulated catalytic beds 36, a product-containing effluent is formed. The effluent 58 comprises ethylbenzene, PEBs, and unreacted benzene. Preferably, the effluent has an outlet temperature of not greater than about 260° C.

The effluent is passed along line 58 from the reactor 14 to a benzene column 60 for recovery and recycling of the unreacted benzene. The benzene column 60 produces a benzene vapor stream 62 that is passed through a heat exchanger 64 and cooled before being directed to an accumulator 66. Light volatiles are vented from the accumulator 66 along line 68. The recycled benzene stream 53 is fluidly communicated from the accumulator 66 and combined with the fresh benzene stream 52 to form the benzene feed stream 54. The benzene-depleted effluent is directed from the benzene column 60 to an ethylbenzene column 68 along line 70 for separation and recovery of the product, ethylbenzene. The ethylbenzene product is passed along line 71 from the ethylbenzene column 68 through a heat exchanger 72 that cools the ethylbenzene product before being directed to the accumulator 74. The cooled ethylbenzene product is removed from the accumulator 74 along line 76. A PEB-rich liquid stream is removed from the ethylbenzene column 68 along line 77 and directed to the PEB column 78 for separation and recovery of PEBs. A flux oil stream is removed from the PEB column 78 along line 79, and a PEB vapor stream is removed along line 80 and cooled via a heat exchanger 82 before being directed to an accumulator 84. A cooled PEB stream is passed from the accumulator 84 along line 86 and combined with benzene from the benzene feed stream 54 along line 88. The combined PEB-benzene stream is introduced into a transalkylation reactor 90 and reacted to generate more ethylbenzene. A product stream obtained from the transalkylation reactor 90 is passed along line 92 to the benzene column 60.

Accordingly, methods and apparatuses for producing ethylbenzene have been described. An alkylator apparatus comprises a reactor that is a multi-fixed bed flow reactor and is configured to receive a benzene stream and a plurality of ethylene streams at a preferably relatively low BE ratio. The reactor comprises at least one group of adjacent thermally-insulated catalyst beds. The benzene stream is combined with one of the ethylene streams in the first pre-bed space to form a feed mixture that is benzene-rich. The group of adjacent thermally-insulated catalyst beds includes a cold bed and a hot bed. The cold bed initially receives the feed mixture at preferably a relatively low inlet temperature. The cold bed contains UZM-8 zeolite-based catalyst. The inventors have found that although the UZM-8 zeolite-based catalyst does not have relatively high activity for the catalytic alkylation of benzene with ethylene, it has very low deactivation at relatively low inlet temperatures. The feed mixture is advanced through the cold bed contacting the UZM-8 zeolite-based catalyst to form an intermediate outlet stream comprising ethylbenzene and unreacted benzene. The heat generated during the reaction causes an increase in temperature as the feed mixture is reacted and advanced through the cold bed to form the intermediate outlet stream. The intermediate outlet stream is advanced from the cold bed to a second pre-bed space and combined with a second ethylene stream to form an intermediate feed mixture that is introduced to the hot bed at an inlet temperature preferably of about 190° C. or greater. The hot bed contains beta zeolite-based catalyst. The intermediate feed mixture is advanced through the hot bed contacting the beta zeolite-based catalyst to form an outlet stream comprising ethylbenzene. The inventors have found that although the beta zeolite-based catalyst has relatively fast deactivation under low inlet temperatures, it is very active and is stable at the higher inlet and processing temperatures associated with the hot bed. Additionally, the amount of beta zeolite-based catalyst use in the hot bed is less than if UZM-8 zeolite-based catalyst was used because of the high activity of the beta zeolite-based catalyst. Therefore, by using UZM-8 zeolite-based catalyst that exhibits lower activity but very low deactivation under low inlet temperatures in the cold bed and using the beta zeolite-based catalyst that exhibits faster deactivation under low inlet temperatures but very high activity and stability at higher inlet temperatures in the hot bed, the reactor can be operated efficiently under relatively low BE feed ratios and low inlet temperatures. Moreover, the frequency of replacing the catalyst in the reactor is reduced in comparison to using the beta zeolite-based catalyst in both the cold and hot beds. Furthermore, the amount of catalyst used overall is reduced in comparison to using the UZM-8 zeolite-based catalyst in both the cold and hot beds.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. A method for producing ethylbenzene using an alkylator apparatus that comprises at least one group of adjacent thermally-insulated catalyst beds, each of the at least one group of adjacent thermally-insulated catalyst beds including a cold bed and a hot bed, the method comprising the steps of:
    introducing a benzene stream and a plurality of ethylene streams to the alkylator apparatus at a predetermined benzene to ethylene ratio of about 3 or less;
    combining the benzene stream with a first ethylene stream of the plurality of ethylene streams to form a first feed mixture;
    contacting the first feed mixture with UZM-8 zeolite-based catalyst in a first cold bed at conditions effective to form a first intermediate outlet stream comprising ethylbenzene and benzene, wherein the first feed mixture is introduced into the first cold bed at a first predetermined inlet temperature of from about 160 to about 190° C.;
    combining the first intermediate outlet stream with a second ethylene stream of the plurality of ethylene streams to form a second intermediate feed mixture; and
    contacting the second intermediate feed mixture with beta zeolite-based catalyst in a first hot bed at conditions effective to form ethylbenzene, wherein the second intermediate feed mixture is introduced into the first hot bed at a second predetermined inlet temperature of from about 190 to about 230° C.,
    wherein the first predetermined inlet temperature is below the second predetermined inlet temperature.

2. The method according to claim 1, wherein the step of introducing the benzene stream includes introducing the benzene stream and the plurality of ethylene streams at the predetermined benzene to ethylene ratio of from about 1.5 to about 3.

3. The method according to claim 1, wherein the step of contacting the second intermediate feed mixture includes forming a second intermediate outlet stream comprising ethylbenzene and benzene, and the method further comprises the steps of:
    cooling and adding a third ethylene stream of the plurality of ethylene streams to the second intermediate outlet stream to form a third intermediate feed mixture;
    contacting a third intermediate mixture with UZM-8 zeolite-based catalyst in a second cold bed at conditions effective to form a third intermediate outlet stream comprising ethylbenzene and benzene, wherein the third intermediate feed mixture is introduced into the second cold bed at a third predetermined inlet temperature;
    combining the third intermediate outlet stream with a fourth ethylene stream of the plurality of ethylene streams to form a fourth intermediate feed mixture; and
    contacting the fourth intermediate feed mixture with beta zeolite-based catalyst in a second hot bed at conditions effective to form ethylbenzene, wherein the fourth intermediate feed mixture is introduced into the second hot bed at a fourth predetermined inlet temperature
    wherein the third predetermined inlet temperature is below the fourth predetermined inlet temperature.

4. The method according to claim 3, wherein the third predetermined inlet temperature is from about 160 to about 190° C.

5. The method according to claim 3, wherein the fourth predetermined inlet temperature is from about 190 to about 230° C.

6. The method according to claim 1, wherein the step of contacting the first feed mixture includes contacting the first feed mixture with the UZM-8 zeolite-based catalyst and substantially no beta zeolite-based catalyst in the first cold bed, and wherein the step of contacting the second intermediate feed mixture includes contacting the second intermediate feed mixture with the beta zeolite-based catalyst and substantially no UZM-8 zeolite-based catalyst in the first hot bed.

* * * * *